(12) United States Patent
Hakky (10) Patent No.: US 8,795,154 B1
(45) Date of Patent: Aug. 5, 2014

(54) PROPULSION INFLATABLE PENILE IMPLANT

(71) Applicant: Said I. Hakky, Largo, FL (US)

(72) Inventor: Said I. Hakky, Largo, FL (US)

(*) Notice: Subject to any disclaimer, the term of this patent is extended or adjusted under 35 U.S.C. 154(b) by 0 days.

(21) Appl. No.: 13/934,895

(22) Filed: Jul. 3, 2013

(51) Int. Cl.
*A61F 5/00* (2006.01)

(52) U.S. Cl.
USPC .................................................. 600/40

(58) Field of Classification Search
USPC ................................................ 600/38–41
See application file for complete search history.

(56) References Cited

U.S. PATENT DOCUMENTS

| | | | | |
|---|---|---|---|---|
| 4,898,158 A | * | 2/1990 | Daly et al. | 600/40 |
| 5,010,882 A | * | 4/1991 | Polyak et al. | 600/40 |
| 5,112,295 A | * | 5/1992 | Zinner et al. | 600/40 |
| 5,437,605 A | * | 8/1995 | Helmy | 600/40 |
| 5,704,895 A | * | 1/1998 | Scott et al. | 600/40 |
| 7,244,227 B2 | * | 7/2007 | Morningstar | 600/40 |

* cited by examiner

*Primary Examiner* — John Lacyk
(74) *Attorney, Agent, or Firm* — Rosenberg, Klein & Lee (57) ABSTRACT

One aspect of the present disclosure relates to an implantable penile prosthesis including an elongated cylinder that includes a pendulous portion configured to move from a non-pressurized state to a pressurized state. A tapered tailoring portion of the elongated cylinder is configured to anchor the elongated cylinder at a base of the penis. The elongated cylinder further includes a flared reservoir portion, at least a portion of which has a diameter that is greater than a diameter of the pendulous portion.

26 Claims, 11 Drawing Sheets

PROPULSION INFLATABLE PENILE IMPLANT

TECHNICAL FIELD

The present disclosure relates generally to an implantable penile prosthesis and, more particularly, to a one-piece implantable penile prosthesis that can be selectively pressurized to effect an erection.

BACKGROUND

Various penile implants have been disclosed in the patent literature and are commercially available for curing erectile impotence. Such devices basically comprise a pair of cylinders, each of which adapted to be implanted in a respective corpus cavernosum of the penis. Each cylinder includes a hollow portion arranged to be pressurized by the pumping of a liquid therein. When the cylinder portions are pressurized the penis assumes an erect, rigid state. The liquid used to inflate the cylinders is provided via respective tubes from a liquid supply reservoir. A pump and a reversible, one-way valve are also included in the prosthesis and are typically arranged to be implanted in the scrotum and/or the abdomen. The pump and valve enable the liquid to be carried from the reservoir into the cylinder to cause the erection when the valve is in a first setting. In order to render the penis flaccid, the valve is arranged to be actuated to enable the liquid to pass through it in the opposite direction so that operation of the pump carries the liquid back into the reservoir.

While the penile implants such as described above have proven suitable for their intended purposes, they nevertheless leave something to be desired from the standpoint of simplicity of construction and ease of operation. In this regard, conventional penile implants require the use of not only the inflatable cylinders, which are to be located within the penis, but also a control valve, pump and reservoir, all of which are implanted within the body remote from the penis. Moreover, operation of such remotely located pump-type penile implants requires the user to first manually operate the valve to its appropriate setting to enable flow from the reservoir to the cylinders and then to manually pump the liquid into cylinders to cause the penis to become erect for sexual intercourse. In order to render the penis flaccid, the valve has to be manually returned to its initial position to enable the liquid to flow therethrough in the opposite direction so that operation of the pump carries the liquid from the cylinders back into the reservoir.

SUMMARY

The present disclosure relates generally to an implantable penile prosthesis and, more particularly, to a one-piece implantable penile prosthesis that can be selectively pressurized to effect an erection.

One aspect of the present disclosure relates to an implantable penile prosthesis comprising an elongated cylinder that includes a pendulous portion configured to move from a non-pressurized state to a pressurized state. A tapered tailoring portion of the elongated cylinder is configured to anchor the elongated cylinder at a base of the penis. The elongated cylinder further includes a flared reservoir portion, at least a portion of which has a diameter that is greater than a diameter of the pendulous portion.

Another aspect of the present disclosure relates to an implantable penile prosthesis comprising an elongated cylinder that includes a pendulous portion configured to move from a non-pressurized state to a pressurized state. The pendulous portion further includes a compressible distal fluid chamber separated from a main fluid chamber by a valve assembly. The valve assembly further includes a housing, a duckbill-umbrella valve operably connected to the housing, and at least one pressure relief valve operably coupled to the housing. A tapered tailoring portion of the elongated cylinder is configured to anchor the elongated cylinder at a base of the penis. The elongated cylinder further includes a flared reservoir portion, at least a portion of which has a diameter that is greater than a diameter of the pendulous portion.

Another aspect of the present disclosure relates to an implantable penile prosthesis comprising an elongated cylinder that includes a pendulous portion configured to move from a non-pressurized state to a pressurized state. The pendulous portion further includes a compressible distal fluid chamber separated from a main fluid chamber by a valve assembly. The valve assembly further includes a housing, a duckbill-umbrella valve operably connected to the housing, and at least one pressure relief valve operably coupled to the housing. A tapered tailoring portion of the elongated cylinder is configured to anchor the elongated cylinder at a base of the penis. The elongated cylinder further includes a flared reservoir portion, at least a portion of which has a diameter that is greater than a diameter of the pendulous portion. The flared reservoir portion further includes a central support member extending therethrough and configured to prevent axial collapse of the pendulous portion during intercourse.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Figure 1A:
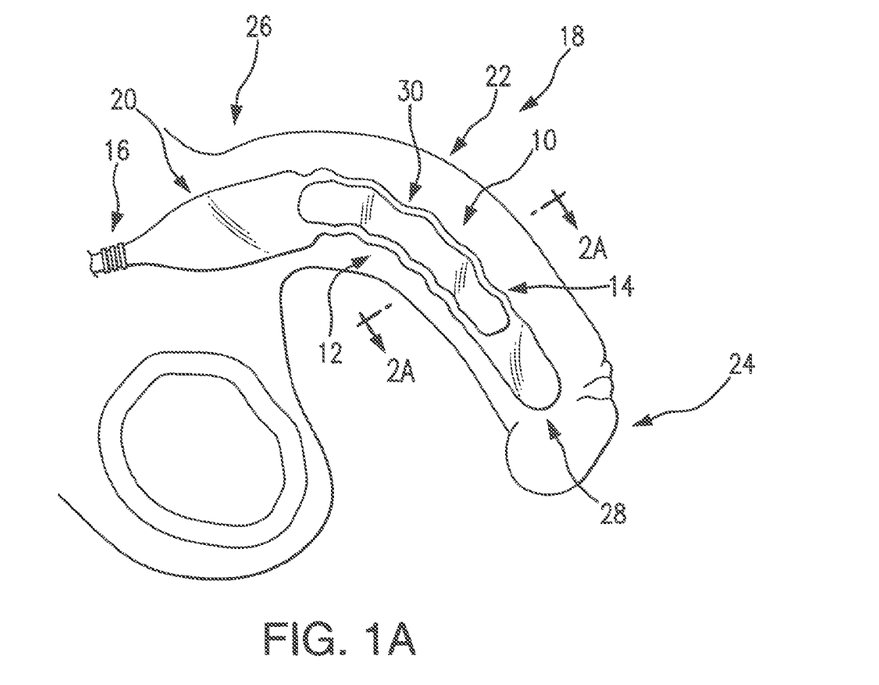
FIG. 1A is a side view, partly in section, of an implantable penile prosthesis in a non-pressurized state constructed in accordance with one aspect of the present disclosure and surgically implanted in a male.
Figure 1B:
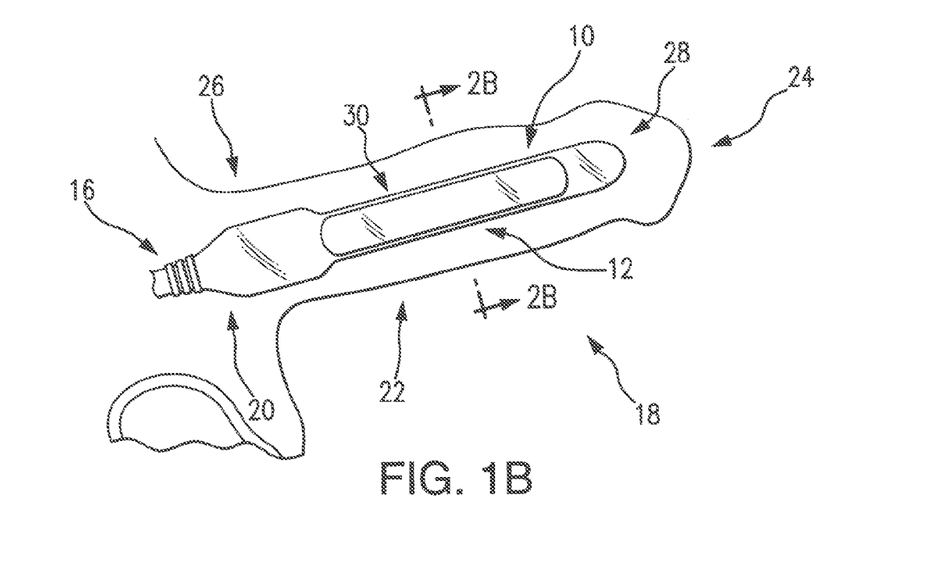
FIG. 1B is a side view similar to FIG. 1A, except that the implantable penile prosthesis is in a pressurized state.
Figure 2A:
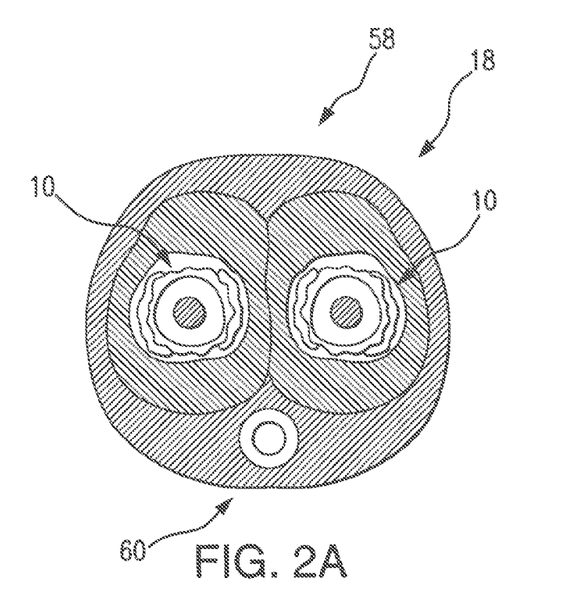
FIG. 2A is an enlarged cross-sectional view taken along Line 2A-2A in FIG. 1A.
Figure 2B:
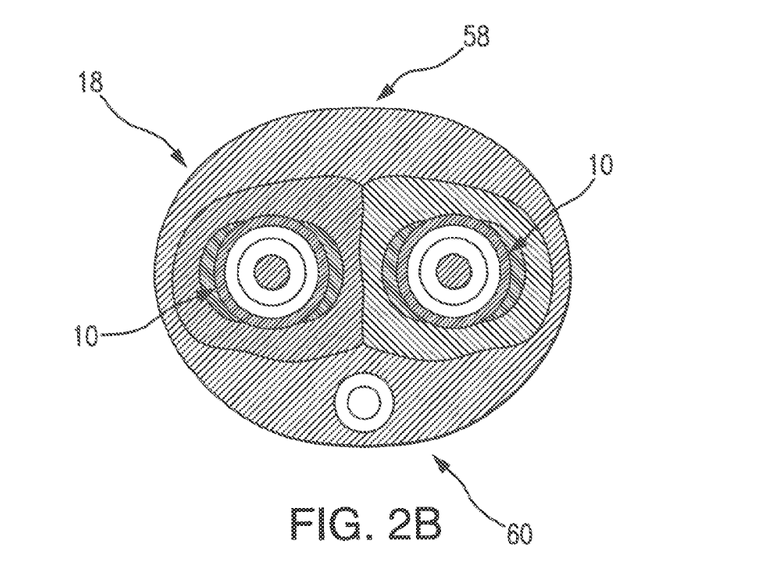
FIG. 2B is an enlarged cross-sectional view taken along Line 2B-2B in FIG. 1B.

One aspect of the present disclosure is illustrated in FIGS. 1A-B and includes an implantable penile prosthesis 10. The penile prosthesis 10 comprises an elongated cylinder 12 including a pendulous portion 14 configured to move from a non-pressurized state (FIG. 1A) to a pressurized state (FIG. 1B), a tapered tailoring portion 16 configured to anchor the elongated cylinder at a base of a penis 18, and a flared reservoir portion 20. In normal practice, two such elongated cylinders 12 are surgically implanted in a male (e.g., to treat impotence or erectile dysfunction). In such a case, each elongated cylinder 12 is surgically implanted longitudinally in a respective corpus cavernosum (FIGS. 2A-B) of the penis 18, with the pendulous portion 14 located within the shaft 22 and distal portion 24 of the penis, and with the tapered tailoring portion 16 located within the proximal portion or base 26 of the penis.

A distal end portion 28 of the elongated cylinder 12 is formed from an elastomeric material, such as medical grade silicone rubber, so that it is selectively compressible (e.g., by tactile force) in either a radial or axial direction. The distal end portion 28 is hollow and includes various components (to be described later) for operation of the penile prosthesis 10. The pendulous portion 14 further includes an inflatable intermediate section 30 that is a generally hollow member having an outer wall formed as a thin sleeve of an elastomeric material, such as a medical grade silicone rubber. The intermediate section 30 is thus constructed to be flexible and flaccid in its normal or non-pressurized state, but is configured to be expanded linearly and radially and made rigid when the penile prosthesis 10 is activated or pressurized to render the penis 18 erect. In such a case, the two sections 28 and 30 making up the pendulous portion 14 of the penile prosthesis 10 act like a cantilevered beam, with the tapered tailoring portion 16 serving to anchor the pendulous portion of the penile prosthesis to the body.

As will be fully appreciated from the description to follow, the penile prosthesis 10 of the present disclosure is a completely self-contained, one-piece unit that does not require the use of remotely implanted reservoir/valve/pump arrangements for causing the penile prosthesis to become erect. Unlike conventional penile implants (e.g., two- and three-piece implants), which require multiple incisions for surgical implantation, the penile prosthesis 10 of the present disclosure requires only one incision (e.g., at the suprapubic area or the penoscrotal junction), therefore requiring less anesthesia time. Advantageously, the penile prosthesis 10 does not require the use of a manually actuatable pump (whether implanted remotely of the elongated cylinder 12 or included within the elongated cylinder itself) to cause the penile prosthesis to become erect. In this regard, the mechanism for effecting the erection using the penile prosthesis 10 operates by selective application of pressure to the distal end portion 28 of the penile prosthesis. Thus, when pressure is applied to the tip or head of the penis 18, the pendulous portion 14 becomes erect and remains erect, yet when the pressure is applied to the shaft 22 of the penis the pendulous portion becomes flaccid. This feature enables a person with an implanted penile prosthesis 10 to selectively and normally control the erection process.

Figure 3A:
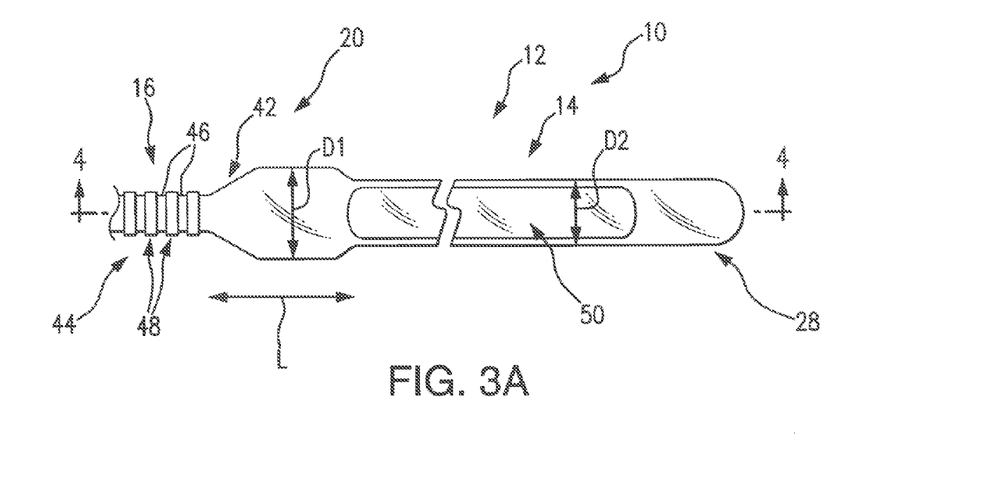
FIG. 3A is a schematic illustration showing a side view of the implantable penile prosthesis in FIG. 1B.
Figure 3B:
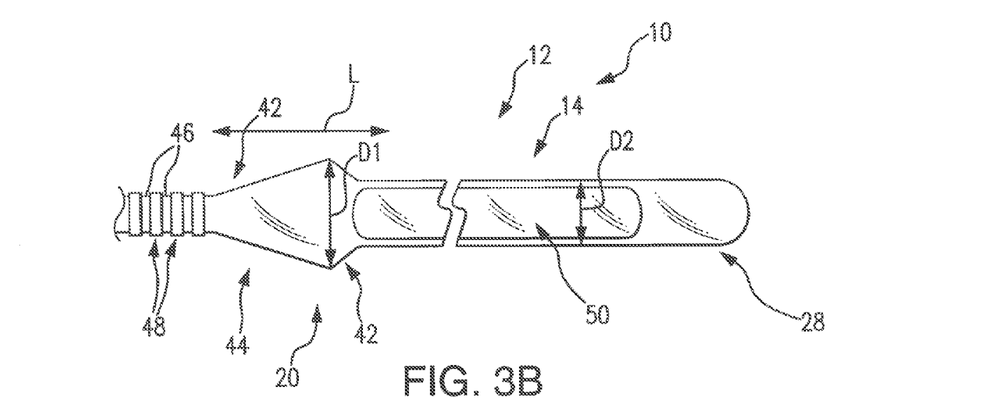
FIG. 3B is a schematic illustration showing an alternative configuration of the implantable penile prosthesis in FIG. 3A.
Figure 3C:
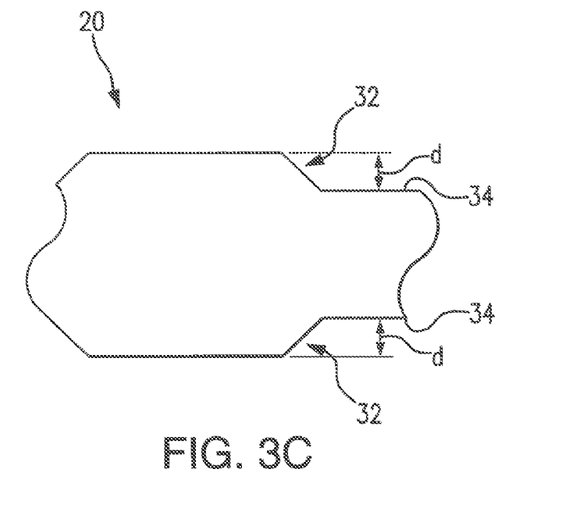
FIG. 3C is an enlarged schematic illustration showing a flared reservoir portion of the penile prosthesis in FIG. 3A.
Figure 3D:
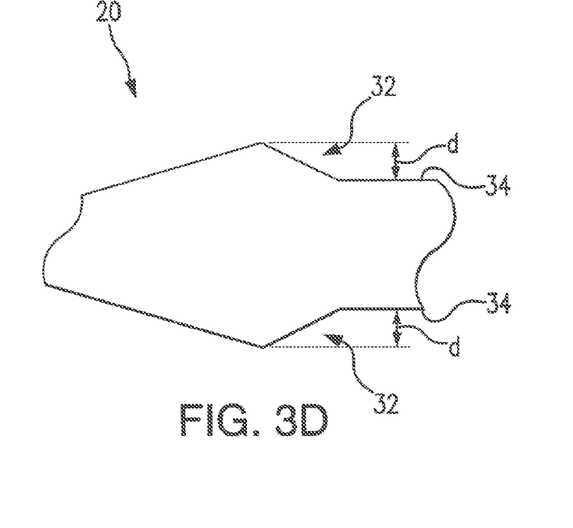
FIG. 3D is an enlarged schematic illustration showing a flared reservoir portion of the penile prosthesis in FIG. 3B.

Referring to FIGS. 3A-D, the flared reservoir portion 20 and the pendulous portion 14 each include a diameter D1 and D2, respectively. The diameter D1 of the flared reservoir portion 20 is greater than the diameter D2 of the pendulous portion 20. In other words, the elongated cylinder 12 does not have a uniform diameter. The diameter D1 of the flared reservoir portion 20 can be substantially the same across the length L thereof (FIG. 3A) or, as shown in FIG. 3B, the diameter D1 can vary across the length L but still remain greater than the diameter D2 of the pendulous portion 14. In one example, the flared reservoir portion 20 can have a length L of about 50 mm. The flared reservoir portion 20 can further include a circumferential, tapered ridge 32 (FIGS. 3C-D) that extends radially outward a distance d from an outer surface 34 of the pendulous portion 14. In one example, the distance d can be about 1 mm. The distance d imparts the flared reservoir portion 20 with a circumference (or girth) that is greater than the circumference (or girth) of the pendulous portion 14. The flared reservoir portion 20 can have a barrel-shaped configuration (FIG. 3A) or a frustoconical configuration as shown in FIG. 3B. Other configurations of the flared reservoir portion 20 are also possible, so long as at least a portion of the flared reservoir portion has a diameter D1 that is greater than the diameter D2 of the pendulous portion 14.

As compared to conventional penile implants having a uniform diameter, the non-uniform diameter of the elongated cylinder 12 imparts the proximal fluid chamber 36 (FIG. 4) of the flared reservoir portion 20 with a greater volume for storing operational fluid (e.g., sterile saline). For example, where the distance d is equal to 1 mm and the length L of the flared reservoir portion 20 is 50 mm, an additional volume of 5 cc (or 10 cc with two prostheses) is available (as compared to conventional penile implants having a uniform diameter). The additional operational fluid volume is sufficient to fully pressurize the main fluid chamber 38 (FIG. 4) as well as the distal fluid chamber 40 during operation of the penile prosthesis 10, which produces a hardness or rigidity only seen with three-piece inflatable penile implants. Therefore, the flared reservoir portion 20 provides the penile prosthesis 10 with the rigidity of a three-piece penile implant but with a less costly and simpler one-piece design.

The tapered tailoring portion 16 (FIGS. 3A-B) of the elongated cylinder 12 comprises a solid body made, for example, of a medical grade silicone rubber and having a cylindrical front portion 42 and a tapered rear portion 44. A plurality of longitudinally spaced, annular recesses 46 is provided in the surface of the rear portion 44. The annular recesses 46 form a plurality of rings 48, which can be spaced apart at a desired uniform or non-uniform distance (e.g., about 10 mm). These recesses 46 serve as convenient locations for severing a portion of the rear portion 44 away from the remainder of the elongated cylinder 12 to configure the penile prosthesis 10 to the appropriate size for the penis 18 into which it will be implanted. For example, the rings 48 can be removed (e.g., cut off) to make the penile prosthesis 10 shorter for patients with a smaller penis. Unlike conventional penile implants, which use rear extenders to tailor the size of the implants, the configuration of the tapered tailoring portion 16 allows the penile prosthesis 10 to be easily customized to the size of the patient's penis 18.

The penile prosthesis 10 additionally includes first and second inflation members 50 and 52 disposed along the medial portions 54 (FIG. 5) of the elongated cylinder 12. Each of the first and second inflation members 50 and 52 can comprise a bladder made, for example, of a flexible yet resilient material (e.g., rubber). Each of the first and second inflation members 50 and 52 includes a lumen 56 capable of receiving an operational fluid. As described below, the lumen 56 of each of the first and second inflation members 50 and 52 is in fluid communication with the main fluid chamber 38 of the pendulous portion 14. The first and second inflation members 50 and 52 (FIGS. 3A-B) can extend longitudinally about the pendulous portion 14 of the elongated cylinder 12. The first and second inflation members 50 and 52 can have any desired shape, such as rectangular, elliptical, square, etc. During pressurization of the penile prosthesis 10, the first and second inflation members 50 and 52 can be inflated to provide additional medial girth to the penis 18 while the girth associated with the dorsal and ventral portions 58 and 60 (FIGS. 2A-B) of the penis 18 will remain the same or slightly decrease, thereby preventing any impediment to semen flow during ejaculation.

Figure 4:
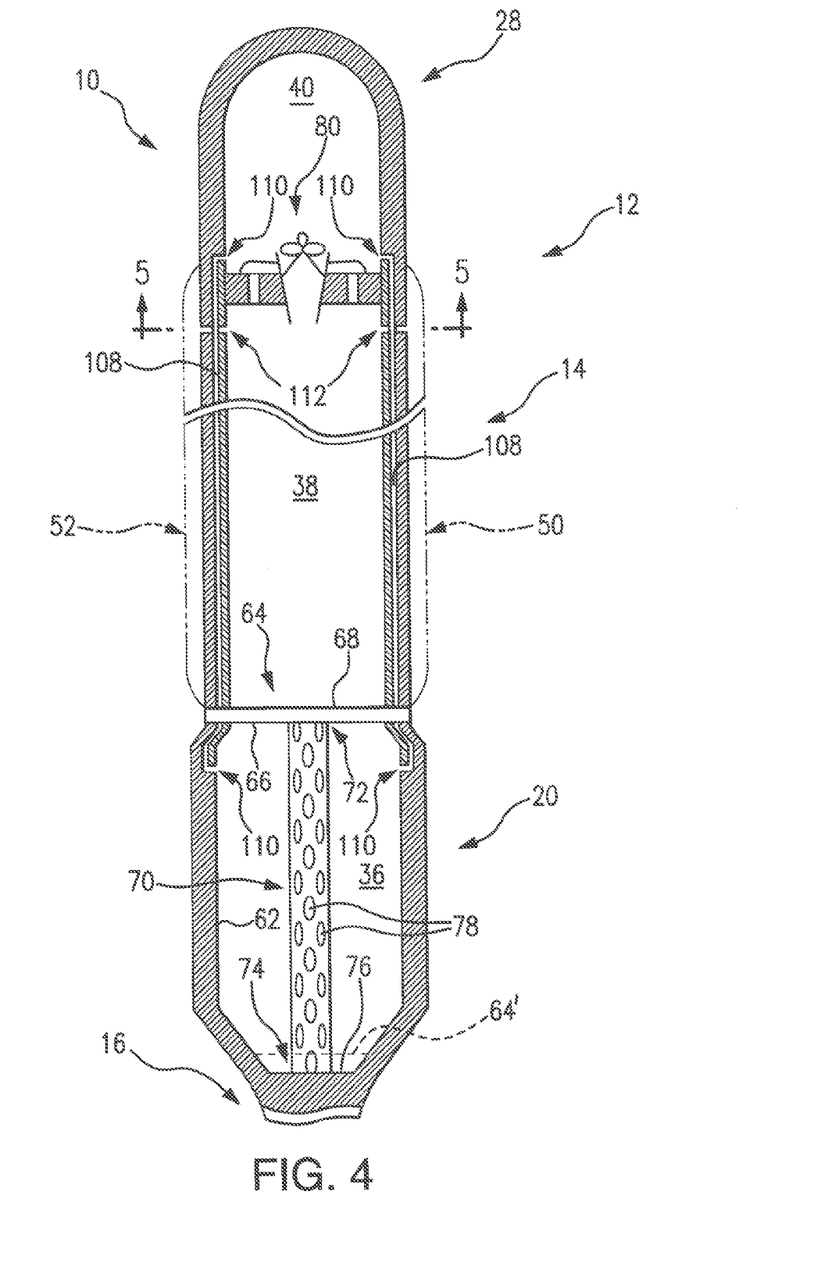
FIG. 4 is a cross-sectional view taken along Line 4-4 in FIG. 3A.

As shown in FIG. 4, the proximal fluid chamber 36 of the flared reservoir portion 20 is defined by an inner wall 62 of the elongated cylinder 12 and a first anchoring plate 64, which creates a hermetic seal between the proximal fluid chamber and the main fluid chamber 38. In some instances, the first anchoring plate 64 can be a disc-shaped member having a diameter that equal to the inner diameter of the pendulous portion 14. The disc-shaped member can be made of a rigid or semi-rigid material, such as a silicone or a medical grade plastic. The first anchoring plate 64 can further include a first surface 66 that is in direct contact with, or is exposed to, the proximal fluid chamber 36, and a second surface 68 that is in direct contact with, or is exposed to, the main fluid chamber.

The proximal fluid chamber 36 additionally includes at least one central support member 70 configured to prevent axial collapse of the pendulous portion 14 during sexual intercourse. The central support member 70 can be made of a resiliently flexible material, such as silicone. The central support member 70 can include oppositely disposed first and second ends 70 and 74. The first end 72 can be directly connected to the first surface 66 of the first anchoring plate 64. The second end 74 can be directly connected to a proximal inner surface 76, which partly defines the proximal fluid chamber 36. Alternatively, a second anchoring plate 64' (shown in broken line form in FIG. 4) can be disposed on the proximal inner surface 76 so that the second end 74 of the central support member 70 is directly connected to the second anchoring plate. The second anchoring plate 64' can be identically or similarly constructed as the first anchoring plate 64. In some instances, the central support member 70 can be a hollow piece of material having any desired shape and including one or more fenestrations 78. Alternatively, the central support member 710 can be a solid piece of material. In one example, the central support member 70 can comprise a hollow tube having one or more fenestrations 78 (e.g., a fenestrated tube).

Figure 6A:
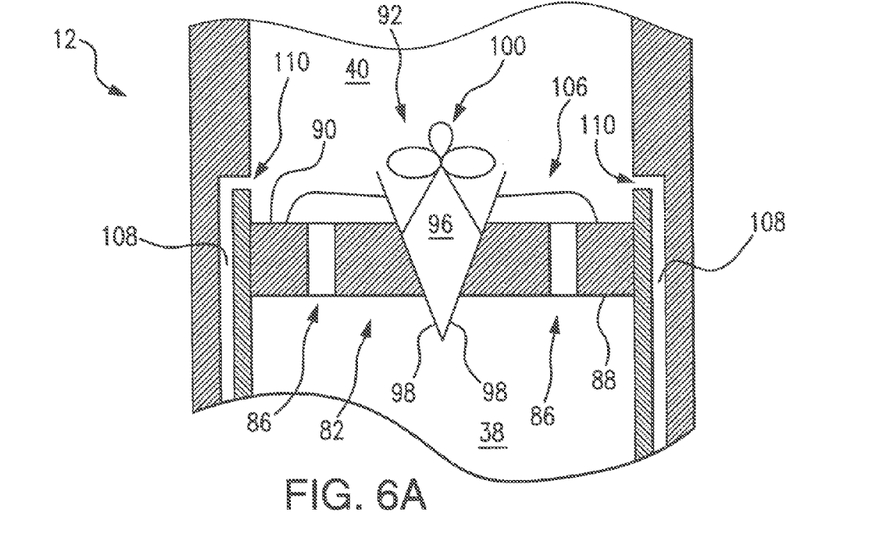
FIG. 6A is an enlarged schematic illustration showing a valve assembly of the implantable penile prosthesis (FIGS. 1A-B) comprising a duckbill-umbrella valve in a closed position.
Figure 6B:
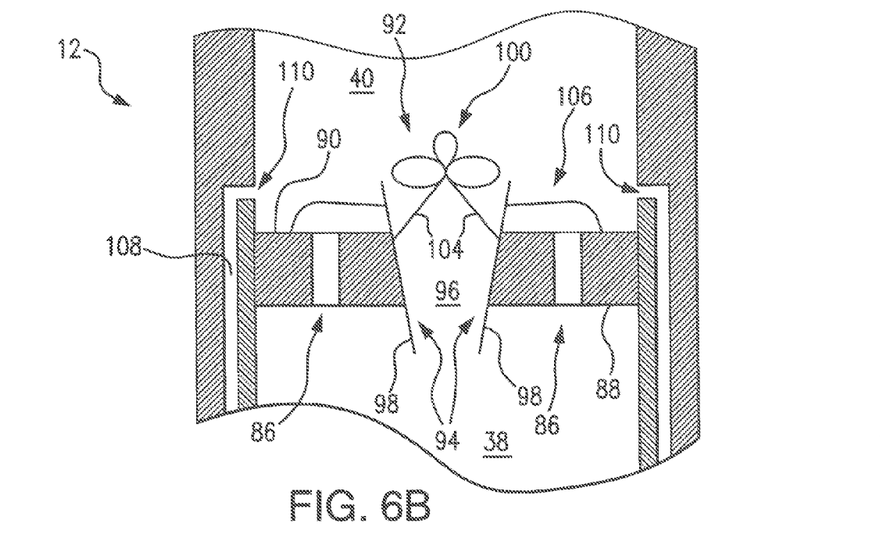
FIG. 6B is an enlarged schematic illustration similar to FIG. 6A, but showing the duckbill-umbrella valve in an open position.
Figure 7A:
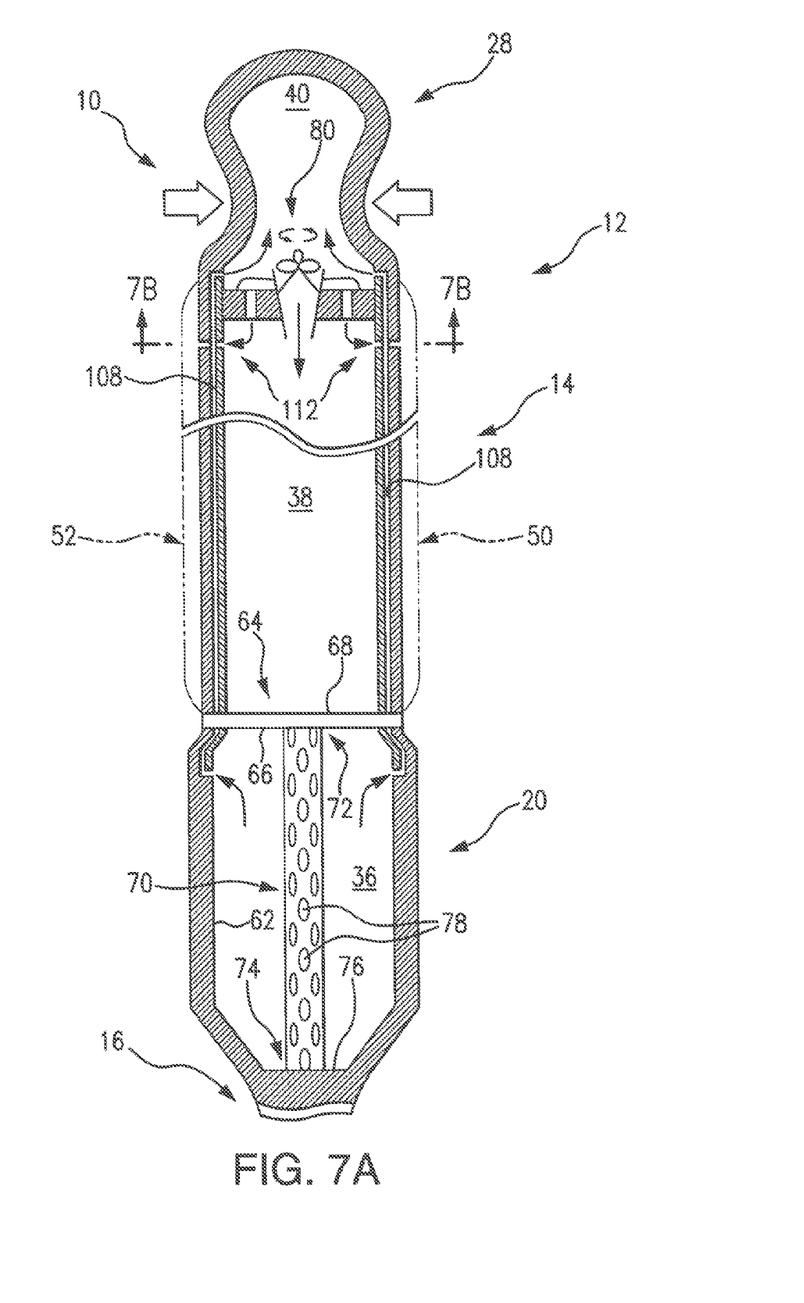
FIG. 7A is a cross-sectional view similar to FIG. 4, but showing compression of a distal fluid chamber so that an operating liquid is flowed into a main fluid chamber of the implantable penile prosthesis (indicated by arrows)
Figure 7B:
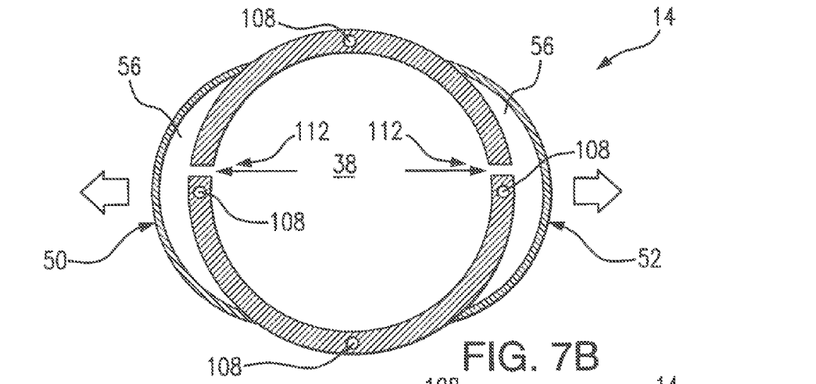
FIG. 7B is a cross-sectional view taken along Line 7B-7B in FIG. 7A.
Figure 8A:
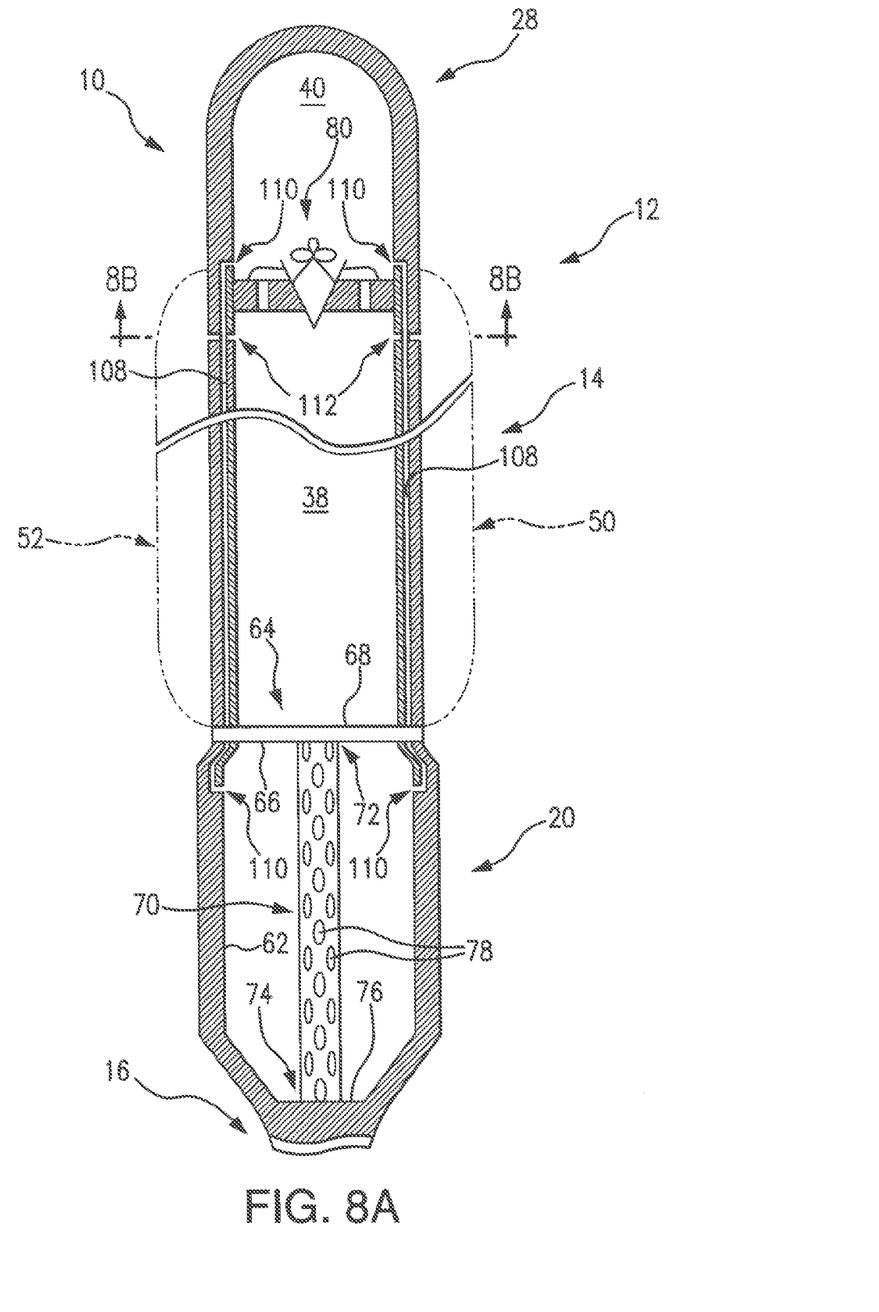
FIG. 8A is a cross-sectional view similar to FIG. 7A, but showing the penile prosthesis in the pressurized state.
Figure 8B:
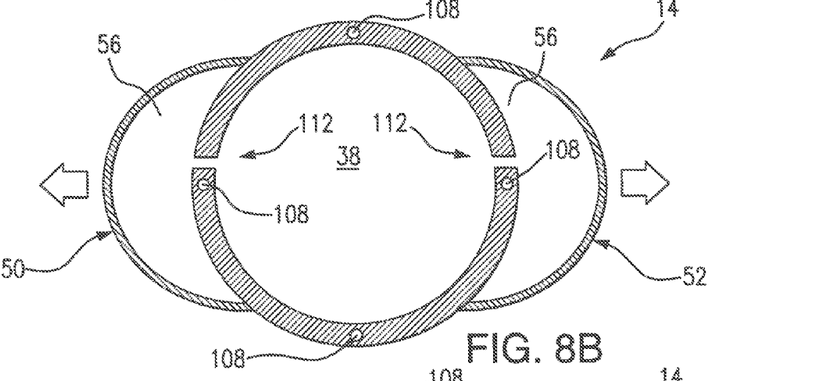
FIG. 8B is a cross-sectional view taken along Line 8B-8B in FIG. 8A.

The compressible distal fluid chamber 40 is separated from the main fluid chamber 38 by a valve assembly 80 (FIGS. 6A-B). The valve assembly 80 can comprise a housing 82, a duckbill-umbrella valve 84 operably connected to the housing, and at least one pressure relief valve 86 that is also operably connected to the housing. In some instances, the housing 82 can include a disc-shaped member (e.g., made of plastic or silicone) having a thickness defined by a first surface 88 and an oppositely disposed second surface 90. The disc-shaped member can have a diameter that is equal to the inner diameter of the pendulous portion 14. The first surface 88 of the housing 82 can be in direct contact with, or be directly exposed to, the main fluid chamber, and the second surface can be in direct contact with, or be directly exposed to, the distal fluid chamber 40. As shown in FIGS. 6A-B, the housing 82 can include two pressure relief valves 86, each of which extends between the first and second surfaces 88 and 90 of the housing. The pressure relief valves 86 allow fluid communication of an operational fluid between the main fluid chamber 38 and the distal fluid chamber 40 at certain times during operation of the penile prosthesis 10. Although two pressure relief valves 86 are shown, it will be appreciated that any number of pressure relief valves can be included as part of the housing 82.

The duckbill-umbrella valve 84 includes a duckbill portion 92 that extends axially through the housing 82 to allow fluid communication between the main fluid chamber 38 and the distal fluid chamber 40 at certain times during operation of the penile prosthesis 10. In some instances, the duckbill portion 92 can include opposable flaps 94 that form a channel 96 therebetween. In a closed configuration (FIG. 6A), opposing distal ends 98 of the flaps 94 are in contact with one another so that operational fluid cannot flow between the main fluid chamber 38 and the distal fluid chamber 40. In an open configuration (FIG. 6B), the distal ends 98 of the flaps 94 are free from contact with one another so that operational fluid can flow through the channel 96. Also included as part of the duckbill portion 92 of the duckbill-umbrella valve 94 is a propeller 100. The propeller 100 is situated at a proximal end 102 of the duckbill portion 92. For example, the propeller 100 can be operably connected to the duckbill portion 92 via one or more strut members 104 that suspend the propeller in (or slightly above) the channel 96. In one example, the propeller 100 can include a three-blade propeller. As compared to four or five blade propellers, the three-blade propeller 100 can provide a more powerful jet during flow of operational fluid from the distal fluid chamber 40 into the main fluid chamber 38.

The duckbill-umbrella valve 84 also includes an umbrella portion 106 configured to sealingly cover each of the pressure relief valves 86 at certain times during operation of the penile prosthesis 10. In some instances, the umbrella portion 106 can include a skirt-like member (not shown in detail) that can be axially displaced to selectively cover or uncover the pressure relief valves 86 (e.g., in response to pressure exerted through the pressure relief valves). The umbrella portion 106 can be made of the same or a different material as the duckbill portion 92. For example, the umbrella portion 106 can be made of a flexible or semi-flexible material, such as plastic or silicone.

The penile prosthesis 10 further includes longitudinal conduits 108 embedded within the wall of the elongated cylinder 12 and configured to convey and operational fluid therethrough. The longitudinal conduits 108 extend between the distal fluid chamber 40 and the proximal fluid chamber 36 so that the distal and proximal fluid chambers are in fluid communication with one another. The distal fluid chamber 40 communicates with the longitudinal conduits 108 via a corresponding set of outlets 110. Similarly, the proximal fluid chamber 36 communicates with the longitudinal conduits 108 via a corresponding set of outlets 110. The elongated cylinder 12 can include two, three, four, or more longitudinal conduits 108. In some instances, the longitudinal conduits 108 can be configured to expand during flow of the operational fluid therethrough so that the respective portion(s) of the wall comprising the elongated cylinder 12 also expands to increase the lateral girth of the penile prosthesis 10.

Figure 5:
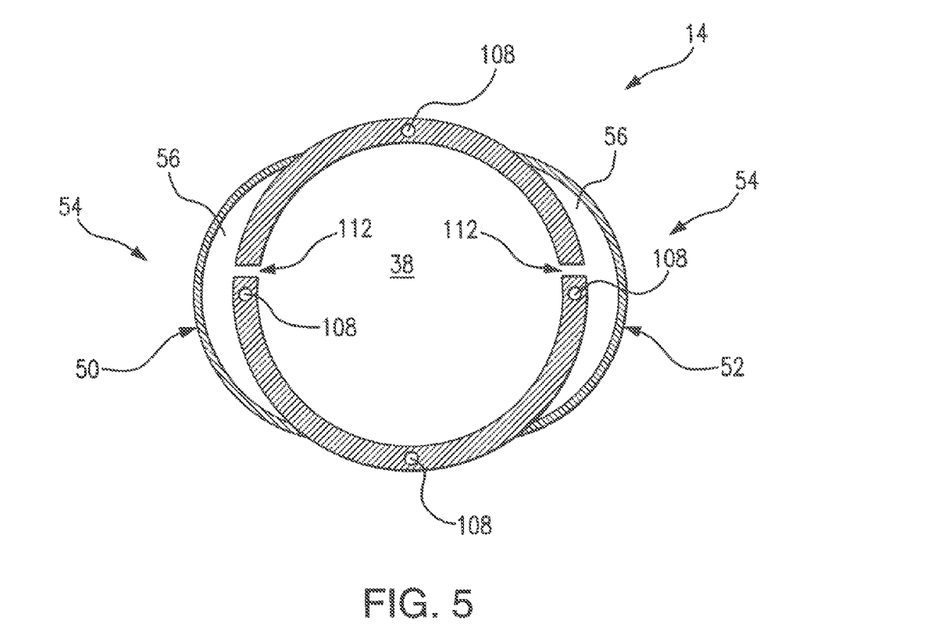
FIG. 5 is a cross-sectional view taken along Line 5-5 in FIG. 4.

The elongated cylinder 12 additionally includes a set of transverse conduits 112. The transverse conduits 112 extend through the wall of the elongated cylinder 12 so that the main fluid chamber 38 is in fluid communication with each of the first and second inflation members 50 and 52. Although only two transverse conduits 112 are shown in FIGS. 4-5, it will be appreciated that the elongated cylinder 12 can be configured with three, four, or more transverse conduits.

Operation of the penile prosthesis 10 is illustrated in FIGS. 7A-9B. Beginning with FIG. 7A, when a male is ready for intercourse, the tip or end portion of the penis 18 can first be squeezed or depressed. Compressing the tip or end of the penis 18 causes the distal fluid chamber 40 to slightly collapse and function like a pump, sending operational fluid contained in the distal fluid chamber through the valve assembly 80 (e.g., the duckbill-umbrella valve 84) into the main fluid chamber 38. The operational fluid is quickly and forcefully flowed through the channel 96 by the action of the propeller 100 (indicated by arrows) into the main fluid chamber 38. As the operational fluid fills the main fluid chamber 38, operational fluid also flows through the transverse conduits 112 into the first and second inflation members 50 and 52 (indicated by arrows). At the same time, operational fluid can flow from the proximal fluid chamber 36, through the longitudinal conduits 108, and into the distal fluid chamber 40 to pressurize the distal end portion 28 of the pendulous portion 14. The main fluid chamber 38 is filled with operational fluid pressure until the main fluid chamber obtains an operational fluid pressure of about 3-5 psi. Upon reaching the operational fluid pressure, the duckbill portion 92 of the duckbill-umbrella valve 84 closes and flow of operational fluid throughout the penile prosthesis 10 is discontinued. Also upon reaching the operational fluid pressure, the first and second longitudinal inflation members 50 and 52 are filled and fully expanded (FIGS. 8A-B). At this point, the penile prosthesis 10 is in its pressurized state and thereby effects an erection.

Figure 9A:
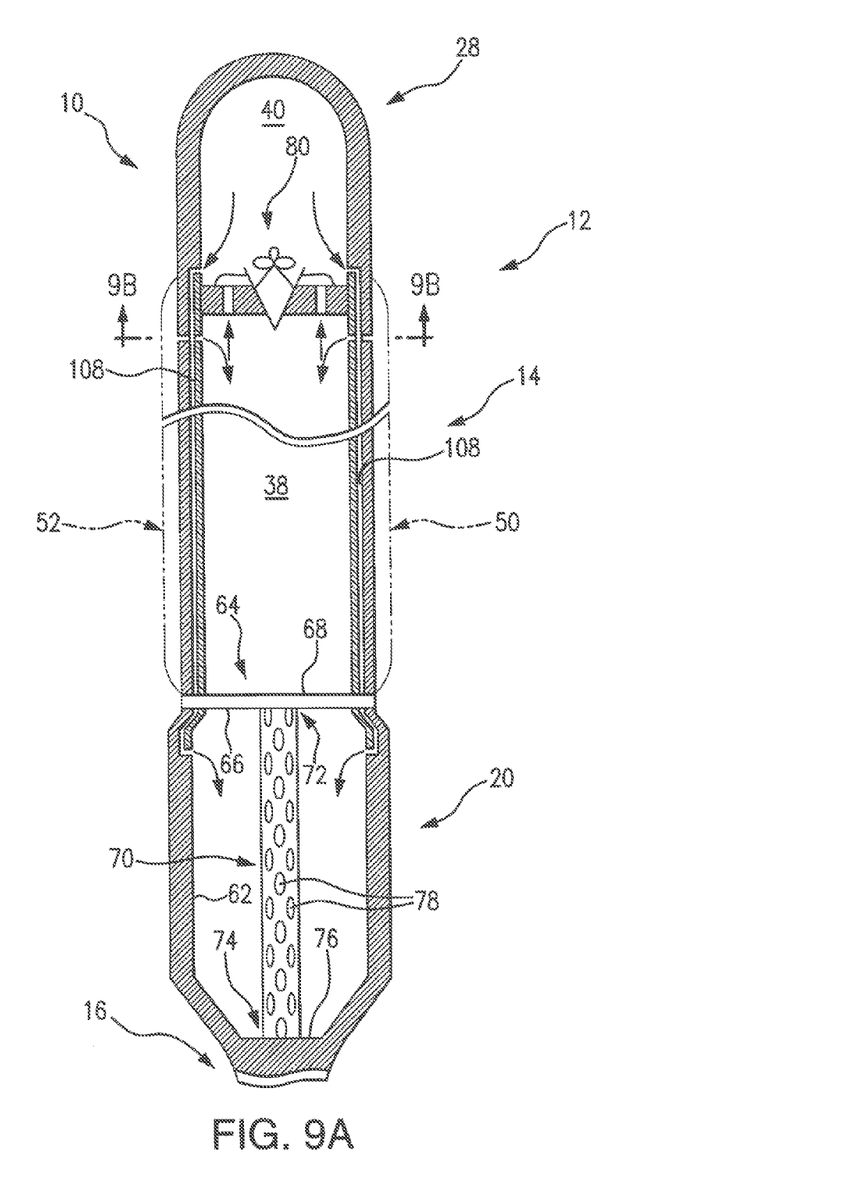
FIG. 9A is a cross-sectional view similar to FIG. 8A, but showing the penile prosthesis transitioning to the non-pressurized state.
Figure 9B:
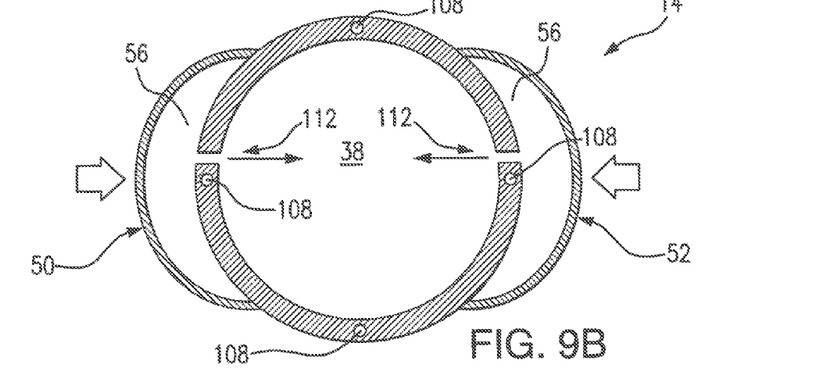
FIG. 9B is a cross-sectional view taken along Line 9B-9B in FIG. 9A.

When the male is ready to return his penis to a normal or flaccid state, pressure can be applied to the shaft 22 of the penis by 18, for example, slightly flexing or bending the shaft. Application of pressure to the shaft 22 causes the pressure within the main fluid chamber 38 to increase above a cut-off level (e.g., about 5 psi). When the internal fluid pressure of the main fluid chamber 38 increases above the cut-off level, the pressure relief valves 86 and the umbrella portion 106 of the duckbill-umbrella valve 84 are actuated so that operational fluid can flow through the pressure relief valves (indicated by arrows in FIG. 9A) into the distal fluid chamber 40. Movement of operational fluid out of the main fluid chamber 38 also causes operational fluid to flow out of the first and second inflation members 50 and 52 into the main fluid chamber (FIG. 9B), thereby deflating the first and second inflation members. Additionally, the duckbill portion 92 of the duckbill-umbrella valve 84 is closed so that the operational fluid does not back flow into the main fluid chamber 38. As the operational fluid flows into the distal fluid chamber 40, operational fluid is flowed through the longitudinal conduits 108 into the proximal fluid chamber 36. Movement of operational fluid from the main fluid chamber 38 into the distal and proximal fluid chambers 40 and 36 causes a decrease in the internal pressure of the pendulous portion 14, thereby transitioning the penile prosthesis 10 to its non-pressurized state and returning the penis 18 to its normal or flaccid state.

From the above description of the present disclosure, those skilled in the art will perceive improvements, changes and modifications. Such improvements, changes, and modifications are within the skill of those in the art and are intended to be covered by the appended claims. All patents, patent applications, and publication cited herein are incorporated by reference in their entirety.

The following is claimed:

1. An implantable penile prosthesis comprising:
an elongated cylinder for disposition within the penis, the cylinder including a pendulous portion configured to move from a non-pressurized state to a pressurized state, a tapered tailoring portion configured to anchor the elongated cylinder at a base of the penis, and a flared reservoir portion, at least a portion of the flared reservoir portion having a diameter that is greater than a diameter of the pendulous portion wherein the pendulous portion further includes first and second inflation members oppositely disposed about first and second lateral portions of the elongated cylinder, respectively.

2. The prosthesis of claim 1, wherein the pendulous portion includes a compressible distal fluid chamber separated from a main fluid chamber by a valve assembly.

3. The prosthesis of claim 2, wherein the valve assembly further comprises:
a housing;
a duckbill-umbrella valve operably connected to the housing; and
at least one pressure relief valve operably connected to the housing.

4. The prosthesis of claim 3, wherein the duckbill-umbrella valve includes a propeller operably connected thereto.

5. The prosthesis of claim 4, wherein the propeller is a three-blade propeller.

6. The prosthesis of claim 2, including an operating liquid in the compressible distal fluid chamber and the main fluid chamber whereby a compression of the distal fluid chamber causes an operating liquid to flow from the distal fluid chamber through the valve assembly into the main fluid chamber.

7. The prosthesis of claim 1, wherein the flared reservoir portion includes a proximal fluid chamber hermetically separated from the main fluid chamber by a first anchoring plate.

8. The prosthesis of claim 7, wherein a central support member extends through the proximal fluid chamber between the first anchoring plate and an oppositely disposed second anchoring plate.

9. The prosthesis of claim 8, wherein the central support member is configured to prevent axial collapse of the pendulous portion during intercourse.

10. The prosthesis of claim 8, wherein the central support member comprises a fenestrated tube.

11. The prosthesis of claim 1, wherein the elongated cylinder includes an outer surface and an oppositely disposed inner surface that collectively define a wall, the elongated cylinder further including:
a set of longitudinal conduits embedded within the wall and extending between the distal fluid chamber and the proximal fluid chamber so that the distal and proximal fluid chambers are in fluid communication with one another; and
a set of transverse conduits extending through the wall so that the main fluid chamber is in fluid communication with each of the first and second inflation members.

12. The prosthesis of claim 1, wherein the tapered tailoring portion has a rigid configuration and comprises a plurality of radially disposed annular recesses for facilitating the sizing of the elongated cylinder to the size of the penis in which the elongated cylinder is to be implanted.

13. The prosthesis of claim 1, including a compressible distal fluid chamber in fluid communication with a main fluid chamber formed within said pendulous portion, and through a set of transverse conduits into the first and second inflation members so that the first and second inflation members are radially expanded responsive to compression of the distal fluid chamber.

14. The prosthesis of claim 13, wherein the first and second inflation members are laterally expanded from a first position to a second position when the compressible distal chamber is compressed, said second position defining an increased lateral girth of the penis devoid of an increase of the dorsal and ventral girth of the penis.

15. The prosthesis of claim 3, wherein a fluid pressure of greater than about 5 psi within the main fluid chamber actuates the at least one pressure relief valve so that the operational fluid flows from the main fluid chamber into the distal chamber, through the set of longitudinal fluid conduits, and into the proximal fluid chamber.

16. The prosthesis of claim 15, wherein flexure of the penis shaft actuates the at least one pressure relief valve.

17. The prosthesis of claim 1, wherein said prostheses is devoid of connection to an external fluid reservoir or pump.

18. An implanted penile prosthesis in the form of an elongated cylinder positioned within the penis, comprising:
    (a) a pendulous portion having a distal end portion defining a distal fluid chamber and a main fluid chamber in fluid communication with said distal fluid chamber;
    (b) a valve mechanism mounted between said main fluid chamber and said distal fluid chamber for selective transmission of fluid therebetween;
    (c) a flared reservoir portion coupled to said pendulous portion of said elongated cylinder, said flared reservoir portion in fluid communication with said distal fluid chamber, said flared reservoir portion being hermetically sealed from said main fluid chamber; and,
    (d) an inflation housing in fluid communication with said main fluid chamber and coupled to said pendulous portion for transverse displacement responsive to fluid transport from said main fluid chamber.

19. The implanted penile prosthesis as recited in claim 18 where at least a portion of said flared reservoir portion includes a flared reservoir portion diameter greater than a pendulum portion diameter when said pendulous portion is in both a pressurized state and in a non-pressurized state.

20. The implanted penile prosthesis as recited in claim 18 where said valve mechanism includes:
    (a) a duckbill-umbrella valve for fluidly coupling said distal fluid chamber to said main fluid chamber; and,
    (b) a pressure relief valve acting in cooperation with said duckbill-umbrella valve for fluid communication between said distal fluid chamber and said main fluid chamber.

21. The implanted penile prosthesis as recited in claim 20 where said duckbill umbrella valve has attached thereto a propeller mechanism for increasing fluid flow through said duckbill umbrella valve.

22. The implanted penile prosthesis as recited in claim 18 where said inflation housing is fluidly coupled to said main fluid chamber through a plurality of transverse conduits through a pendulous portion wall whereby fluid is reversibly transported into said inflation housing.

23. The implanted penile prosthesis as recited in claim 22 where said inflation housing includes at least two inflation members secured to said elongated cylinder positioned on opposing sides of said pendulous portion wall.

24. The implanted penile prosthesis as recited in claim 18 where said elongated cylinder includes a plurality of longitudinally directed conduits extending through a wall of said elongated cylinder for fluid communication between said flared reservoir portion and said distal fluid chamber.

25. An implanted penile prosthesis comprising:
    an elongated cylinder for disposition within the penis, the cylinder including a pendulous portion configured to move from a non-pressurized state to a pressurized state, a tapered tailoring portion configured to anchor the elongated cylinder at a base of the penis, and a flared reservoir portion, at least a portion of the flared reservoir portion having a diameter that is greater than a diameter of the pendulous portion, said pendulous portion including a main fluid chamber separated from a distal fluid chamber by a valve assembly, said valve assembly including a duck-bill umbrella valve operably connected to said distal fluid chamber and said main fluid chamber, said duckbill valve assembly further including at least one pressure relief valve operable connected to said distal fluid chamber and said main fluid chamber, said duckbill-umbrella valve including a propeller member connected thereto.

26. An implantable penile prosthesis comprising:
    an elongated cylinder for disposition within the penis, the cylinder including a pendulous portion configured to move from a non-pressurized state to a pressurized state, a tapered tailoring portion configured to anchor the elongated cylinder at a base of the penis, and a flared reservoir portion, at least a portion of the flared reservoir portion having a diameter that is greater than a diameter of the pendulous portion,
    wherein the elongated cylinder includes an outer surface and an oppositely disposed inner surface that collectively define a wall, the elongated cylinder further including:
        a set of longitudinal conduits embedded within the wall and extending between the distal fluid chamber and the proximal fluid chamber so that the distal and proximal fluid chambers are in fluid communication with one another; and
        a set of transverse conduits extending through the wall so that the main fluid chamber is in fluid communication with each of the first and second inflation members.

* * * * *